United States Patent [19]

Bhasin et al.

[11] Patent Number: 4,916,243
[45] Date of Patent: Apr. 10, 1990

[54] CATALYST COMPOSITION AND PROCESS FOR OXIDATION OF ETHYLENE TO ETHYLENE OXIDE

[75] Inventors: Madan M. Bhasin, Charleston; Paul C. Ellgen, Saint Albans; Charles D. Hendrix, South Charleston, all of W. Va.

[73] Assignee: Union Carbide Chemicals and Plastics Company Inc., Danbury, Conn.

[21] Appl. No.: 32,911

[22] Filed: Apr. 1, 1987

Related U.S. Application Data

[63] Continuation of Ser. No. 763,273, Aug. 7, 1985, abandoned, which is a continuation of Ser. No. 497,231, May 23, 1983, abandoned, which is a continuation of Ser. No. 116,292, Feb. 13, 1980, abandoned, which is a continuation-in-part of Ser. No. 21,727, Mar. 20, 1979, abandoned.

[51] Int. Cl.[4] .............................................. C07D 301/10
[52] U.S. Cl. .................................................... 549/534
[58] Field of Search ........................................ 549/534

[56] References Cited

U.S. PATENT DOCUMENTS

| | | | |
|---|---|---|---|
| 3,962,136 | 6/1976 | Nielsen et al. | 549/534 |
| 4,168,247 | 9/1979 | Hayden et al. | 549/534 |
| 4,207,210 | 6/1980 | Kilty | 549/534 |
| 4,212,772 | 7/1980 | Mron et al. | 549/534 |
| 4,248,740 | 2/1981 | Mitsuhata et al. | 549/534 |

FOREIGN PATENT DOCUMENTS

0854904 11/1977 Belgium.
0867185 11/1978 Belgium.

*Primary Examiner*—Richard L. Raymond
*Assistant Examiner*—Mark W. Russell
*Attorney, Agent, or Firm*—Morris N. Reinisch

[57] ABSTRACT

This invention relates to a supported silver catalyst for the manufacture of ethylene oxide which contains a combination of (a) cesium and (b) at least one other alkali metal selected from the group consisting of lithium, sodium, potassium and rubidium, which combination comprises (a) and (b) in amounts in relation to the amount of silver therein sufficient to increase the efficiency of ethylene oxide manufacture to a value greater than the efficiencies obtainable under common conditions from respective catalysts which are the same as said catalyst except that instead of containing both (a) and (b), one contains the respective amount of (a), and the other contains the respective amount of (b). There is also described herein a process of making such catalyst and a process for producing ethylene oxide with such catalyst.

11 Claims, 2 Drawing Sheets

CATALYST COMPOSITION AND PROCESS FOR OXIDATION OF ETHYLENE TO ETHYLENE OXIDE

This application is a continuation of prior U.S. application Ser. No. 763,273 filing date Aug. 7, 1985 which is a continuation of application now abandoned Ser. No. 497,231 filing date May 23, 1983 which is a continuation of application now abandoned Ser. No. 116,292 filing date Feb. 13, 1980 now abandoned which is a continuation-in-part of Ser. No. 021,727 filed Mar. 20, 1979 now abandoned.

This invention is concerned with silver catalysts, their manufacture and their use in the manufacture of ethylene oxide. The catalyst of this invention comprises a supported silver catalyst. The catalyst contains a combination of (a) cesium and (b) at least one other alkali metal selected from the group consisting of lithium, sodium, potassium and rubidium, wherein (a) and (b) are present in amounts in relation to the amount of silver therein sufficient to increase the efficiency of the ethylene oxide manufacture to a value greater than the efficiencies obtainable under common operating conditions from respective catalysts which are the same as said catalyst except that instead of containing both (a) and (b), one contains the respective amount of (a), and the other contains the respective amount of (b). Thus, the catalyst, when utilized in the manufacture of ethylene oxide, contains a combination of cesium and one or more other alkali metals (excluding francium) in an amount which achieves a synergistic result as defined herein. In addition, the process of this invention defines such synergism as a function of the silver content of the catalyst. Thus, for any given amount of silver in the catalyst, the present invention provides the appropriate correlation of alkali metal and silver whereby particular combinations of cesium and one or more other alkali metals may be selected which achieve efficiencies in the manufacture of ethylene oxide which exceed the higher efficiency obtainable with such amount of silver when in combination with the respective amount of either cesium or the other alkali metals in such mixture The manufacture of ethylene oxide by the reaction of oxygen or oxygen-containing gases with ethylene in the presence of a silver catalyst is an old and very well developed art. For example, U.S. Pat. No. 2,040,782, patented May 12, 1936, describes the manufacture of ethylene oxide by the reaction of oxygen with ethylene in the presence of silver catalysts which contain a class of metal promoters. In U.S. Pat. No. Re. 20,370, dated May 18, 1937, Leforte discloses that the formation of olefin oxides may be effected by causing olefins to combine directly with molecular oxygen in the presence of a silver catalyst From that point on, the prior art has focused its efforts on improving the catalyst's efficiency in producing ethylene oxide.

In characterizing this invention, the terms "conversion", "selectivity", and "yield" are employed as defined in U.S. Pat. No. 3,420,784, patented Jan. 7, 1969, at column 3, lines 24-35 inclusive. This definition of "selectivity" is consistent with that disclosed in U.S. Pat. No. 2,766,261 at column 6, lines 5-22, and U.S. Pat. No. 3,144,916, lines 58-61. The definitions of "yield" and "conversion" have more varied meaning in the art and are not to be employed as defined, for example, in the aforementioned U.S. Pat. No. 2,766,261. The terms "efficiency" and "selectivity" as used throughout the specification and claims are intended to be synonymous.

Silver catalysts employed in the manufacture of ethylene oxide have undergone significant changes since their initial period of development. As reported by the art, silver particles were first deposited upon support materials with little attention being paid to support properties, such as surface area, pore volume and chemical inertness. As the art evolved, there developed special technologies related to carriers or supports containing silver that were more effective for the reaction of ethylene with oxygen to produce ethylene oxide. Today, most supports for the silver catalysts are particulate materials which can be loaded in the interior of a reactor wherein the reacting gases and the gaseous products of the reaction are capable of flowing in and about these particulate materials to pass through the reactor and be recovered. The shape of the support is a variable factor and the particular shape selected is peculiar to the reactor employed, the gas flow required, and the surface area which is desired for the optimization of the reaction with other factors also being considered.

The carriers that have been employed are typically made of inorganic materials, generally of a mineral nature. In most cases, the preferred carrier is made of alpha-alumina, such as has been described in the patent literature: see for example, U.S. Pat. Nos. 2,294,383; 3,172,893; 3,332,887; 3,423,328; and 3,563,914.

The silver that is deposited on these carriers is typically in the form of small particles. The patent literature indicates that the size of the silver is a factor in the effectiveness of the catalyst and in most cases fine particle silver is obtained utilizing the standard processes in the art; see for example, U.S. Pat. Nos 2,554,459; 2,831,870; 3,423,328 (specifies that silver particles of 150-400 angstroms are employed); 3,702,259 (disclosed a preparation procedure for forming silver particles less than 1 micron in diameter) and 3,758,418 (discloses silver particles having a diameter less than 1000 angstroms).

The deposition of silver onto the carrier can be achieved by a number of techniques but the two techniques which are most frequently employed involve, in one case, the impregnation of the support with a silver solution followed by heat treatment of the impregnated support to effect deposition of the silver on the support and, in the other case, the coating of the silver on the support by the precipitation of silver or the preformation of silver into a slurry such that the silver particles are deposited on the support and adhere to the support surface when the carrier or support is heated to remove the liquids present. These various procedures are exemplified in various U.S. patents such as U.S. Pat. Nos. 2,773,844; 3,207,700; 3,501,407; and 3,664,970 (see British Patent No. 754,593), and 3,172,893.

The surface area provided by the support has been the subject of considerable interest in the development of silver catalysts. Disclosures concerning the surface area of the catalyst carrier can be found in U.S. Pat. No. 2,766,261 (which discloses that a surface area of 0.002-10 m$^2$/gm is suitable); U.S. Pat. No. 3,172,893 (which depicts a porosity of 35-65% and a pore diameter of 80-200 microns); U.S. Pat. No. 3,725,307 (which depicts a surface area of less than 1 m$^2$/gm and an average pore diameter of 10-15 microns); U.S. Pat. No. 3,664,970 (which utilizes a support having a minimum porosity of about 30%, at least 90% of the pores having diameters in the range of 1-30 microns, and the average of such diameters being in the range of 4–10 microns); and U.S. Pat. No. 3,563,914 (which utilizes a catalyst support having a surface area of less than 1 m$^2$/gm, a volume of 0.23 ml/gm and a particle size between 0.074 and 0.30 mm).

In the very earliest developments of silver catalysts for the manufacture of ethylene oxide, it has been determined that a number of metals when present in combination with the silver could act as promoters of the silver catalyst. These materials in themselves are not catalysts but contribute to enhance the rate or amount of oxide production. One of the problems in determining whether or not these metals act as promoters is the nature of the reaction itself. The reaction between oxygen and ethylene to form ethylene oxide is a highly exothermic reaction. However, even more exothermic than that reaction is the combustion of ethylene or ethylene oxide to carbon dioxide. These reactions occur simultaneously and the critical factor in determining the effectiveness of the over-all process is the measure of control one has over these two competing reactions. Inevitably, a material which enhances the production of ethylene oxide might also be considered a material which inhibits the complete combustion of ethylene to ethylene oxide to carbon dioxide. Thus, there is a problem in defining whether that material which is termed as a promoter is in fact an inhibitor of the combustion reaction. It is well known that there are materials which when added to the reaction result in less carbon dioxide being formed and such materials are termed inhibitors. There are also materials which when provided with the catalysts result in greater production of ethylene oxide and those materials are termed promoters. Whether the latter materials are in reality inhibitors or promoters seems to be an irrelevant issue. What is significant is that the outcome of the reaction is favorable to the production of ethylene oxide. For that reason, when determining or characterizing a catalytic process for producing ethylene oxide a significant factor entering into or qualifying that process is the selectivity of the process to produce ethylene oxide, selectivity being as defined previously.

The use of alkali metals as promoters for the silver catalyzed production of ethylene oxide is extremely well known in the art. As far back as U.S. Pat. No. 2,177,361 issued Oct. 1939 there is found a teaching of the use of alkali metals in silver catalysts. U.S. Pat. No. 2,238,471 discloses that lithium was very desirable as a promoter but that potassium and cesium were detrimental. The examples of that patent utilize essentially 10% by weight of potassium hydroxide or cesium hydroxide to the silver oxide employed in making the catalyst. Later, U.S. Pat. No. 2,404,438 stated that sodium and lithium were effective promoters for this reaction. Essentially the same teaching could be found in U.S. Pat. No. 2,424,084. U.S. Pat. No. 2,424,086 generalized about alkali metals as promoters and specified sodium in particular. In U.S. Pat. No. 2,671,764, the patentees believed that alkali metals in the form of their sulfates would be effective as promoters for such silver catalysts. In particular, the patentees stated that sodium, potassium, lithium, rubidium or cesium sulfates may be used as promoters. U.S. Pat. No. 2,765,283 described the pretreatment of a support with a dilute solution of a chlorine containing compound and indicated that such chlorine compounds should be inorganic. Particular illustrations cited of suitable inorganic chlorine compounds included sodium chloride, lithium chloride and potassium chlorate This patent specified that the amount of the inorganic chlorine containing compound which is deposited on the catalyst support is from 0.0001% to 0.2% by weight, based on the weight of the support. U.S. Pat. No. 2,615,900 to Sears describes the use of metal halide in the treatment of the supported catalyst and specifies that such halides can be of alkali metals such as lithium, sodium, potassium, and cesium. The metal halide is present in the range of 0.01% to 50% based upon the weight of metallic silver. The patent also specifies that mixtures of the individual metal halides generally classified in the patent may be used to advantage to enhance the break-in period of a new catalyst composition while at the same time maintain a moderate but steady activity of the catalyst over an extended period of time during normal operation. Thus, one particular metal halide treated catalyst would provide a short-term high initial activity whereas another of the metal halides would provide a longer term moderate activity for the catalyst. This patent takes the position that the metal halides which are provided in the catalyst serve to inhibit the combustion of ethylene to carbon dioxide and thus classifies these materials as catalyst depressants or anticatalytic materials. U.S. Pat. No. 2,709,173 describes the use of a silver catalyst for making ethylene oxide in which there are provided simultaneously with the introduction of the silver catalyst to the solid support any of the alkali metal halides such as lithium, sodium, potassium, and rubidium compounds of chlorine, bromine and iodine, to enhance the overall production of ethylene oxide The patent specifies small amounts "of less than about 0.5% are desirable". In particular the patent emphasizes "proportions of alkali metal halide within the range of about 0.0001 to about 0.1%" are most preferred. The patent states that "although the preferred catalyst composition contains a separate promoter it is not always necessary since during preparation of the catalyst the alkali metal halide may be converted to some extent to the corresponding alkali metal oxide which acts as a promoter". U.S. Pat. No. 2,766,261 appears to draw from the teachings of U.S. Pat. No. 2,238,474 in that cesium and potassium are said to be detrimental in silver catalysts; sodium and lithium are suggested as useful promoters. However, U.S. Pat. No. 2,769,016 finds that sodium, potassium and lithium are promoters when used in the silver catalysts. This latter patent also recommends the pretreatment of the support with dilute solutions of sodium chloride, lithium chloride or potassium chlorate. U.S. Pat. No. 2,799,687 to Gould et al states that the addition of metal halides within the range described by Sears in U.S. Pat. No. 2,615,900 is not productive of optimum results. This is said to be especially true in the case of alkali metal halides, particularly the chloride and fluoride of sodium and potassium. The patentees recommend that the inorganic halide component of the catalyst be maintained within the range of 0.01–5 weight percent, preferably 0.01 to 0.1 weight percent, based on the weight of the "silver oxidative catalytic component", i.e., the silver salt transformed into elemental silver. U.S. Pat. No. 3,144,416 mentions a variety of metals as promoters and one of them is cesium. U.S. Pat. No. 3,258,433 indicates that sodium is an effective promoter. U.S. Pat. No. 3,563,913 recommends the use of alkali metals such as lithium compounds as promoters. The preferred amount of promoting material is said to be about 0.03 to 0.5%, by weight, of metal oxide based on the weight of the support. U.S. Pat. No. 3,585,217 states that alkali metal chlorides "are known to counteract the formation of carbon dioxide" and "may be incorporated into the catalyst". U.S. Pat. No. 3,125,538 discloses a supported silver catalyst containing a coincidentally deposited alkali metal selected from among potassium, rubidium and cesium in a specified gram atom ratio relative to silver. The weight of silver is preferably 2–5% by weight, of the catalyst. The patentees characterize this catalyst as being especially suitable for the reaction of nitric oxide with propylene. U.S. Pat. Nos. 3,962,136 and 4,012,425 disclose the identical catalyst as being useful for ethylene oxide production. U.S. Pat. No. 3,962,136 describes the coincidental deposition of alkali metal with the silver on the support, the alkali metals being present in their final form on the support in the form of an oxide in which the oxide consists of cesium, rubidium or mixtures of both, optionally combined with a minor amount of an oxide of potassium. The amount of such oxide is from about $4.0 \times 10^{-5}$ gew/kg to about $8.0 \times 10^{-3}$ gew/kg of total catalyst However, U.S. Pat. No. 4,010,115, patented Mar. 1, 1977, distinguishes itself by employing as the oxide of the alkali metal the oxide of potassium optionally combined with a minor amount of an oxide of rubidium or cesium. Application Ser. No. 317,349, filed Dec. 21, 1972, which is a parent to U.S. Pat. Nos. 3,962,136 and 4,010,115, and others, contains some interesting data deserving of comment. According to example 2 which contains some comparative experiments, there is described the manufacture of a catalyst which contains 310 parts per million by weight of coincidentally-added potassium and that catalyst when employed as an ethylene oxidation catalyst was found to be inactive for the production of ethylene oxide Even so, we find that that amount of potassium in the catalyst lies within the range disclosed in U.S. Pat. No. 4,010,115 to be effective for the production of ethylene oxide, although no data is shown in the patent to support that view.

Belgium Patent No. 821,439, based upon British Patent Specification No. 1,489,335, discloses that a catalyst can be made that is equivalent to that produced in U.S. Pat. Nos. 3,962,136, 4,012,425, and 4,010,115 to Neilsen et al, by varying the procedure by which the alkali metal is supplied to the support. In the Belgium Patent and its British equivalent, a porous refractory support of a specified surface area is first impregnated with an alkali metal to deposit it on the support material in specified quantities (both the quantities and the nature of the porous support being equivalent to that which is set forth in the aforementioned Nielsen et al U.S. patents) the support is then dried to fix the alkali metal and thereafter the silver is supplied to the support. This procedure is a sequential deposition of the alkali metal promoter and the silver catalyst and yet essentially the same type of catalyst was produced by the simultaneous deposition of alkali metal and silver as evidenced by a comparison of the data in the examples of the Belgium Patent with the data set forth in the aforementioned Nielsen et al U.S. patents. The criticality in the method of deposition of alkali metal upon the support appears doubtful in the face of that type of disclosure and the disclosure of U.S. Pat. Nos. 4,033,903 and 4,125,480 which describe subjecting a used silver-containing catalyst with a post-addition of one or more of potassium, rubidium or cesium. Apparently such treatment regenerates the catalyst's ability to enhance selectivity to ethylene oxide. Another patent which tends to indicate that a post-addition of alkali metal such as cesium gives results equivalent to either pre-addition or simultaneous addition is U.S. Pat. No. 4,066,575.

U.S. Pat. No. 3,962,136 and its companion patents were derived from U.S. patent application Ser. No. 216,188, filed Jan. 7, 1972, now abandoned. U.S. Pat. No. 3,962,136 discloses that the "highest level of selectivity obtainable with potassium modified catalysts at other-wise comparable conditions typically is lower than that obtainable with rubidium or cesium-modified catalysts" (see column 2, lines 38–42). U.S. application Ser. No. 216,188 contains a drawing which depicts the relative effectiveness of rubidium, cesium and potassium to enhance the selectivity of ethylene oxide when utilized in a silver catalyst. The drawing shows that the curve C which represents cesium addition provides the greatest degree of enhancement of selectivity while curve B which represents rubidium addition is intermediate and superior to potassium addition represented by curve A. In an amendment filed on Apr. 11, 1975, in U.S. application Ser. No. 480,896, filed June 19, 1974, which is a parent application to U.S. Pat. No. 4,010,115, the applicant urges that the invention and claims do not involve "synergistic effects with the use of mixtures" of the alkali metals. The same statement was made in the amendment received on Apr. 11, 1975 in U.S. patent application Ser. No. 471,398 filed May 20, 1974, which is the parent application to U.S. Pat. No. 4,012,425.

German Offenlegungsschrift No. 2,640,540 discloses in its examples a silver catalyst for ethylene oxide production containing sodium and either potassium, rubidium or cesium. Table I of this disclosure provides the alkali content of all catalysts prepared in the examples, many of which contain sodium, potassium and cesium. A footnote to the Table states that the presence of potassium in all catalysts tested (except for one which was free of cesium) was due to impurities present in the support, the level of such impurities being below that specified as being useful for the invention. The disclosure does not suggest that cesium may be combined with potassium and/or sodium to advantage nor does the efficiency data provided in the Table demonstrate an synergistic interaction of cesium with sodium or the potassium impurities in the catalysts.

Japanese Application Publication Disclosure No. 95213/75 is directed to a process for producing ethylene oxide using a catalyst composition comprising silver, barium, potassium and cesium in specified atomic ratios. Table I of this disclosure summarizes the efficiencies achieved with the various catalyst compositions of the examples. No synergism with cesium and potassium was demonstrated by any of the cesium-potassium-barium mixtures of the examples. Indeed, a comparison of some examples among Table I appears to demonstrate the absence of a cesium-potassium synergism, namely, the efficiency achieved with a cesium-potassium mixture is shown to be lower than the efficiency achieved with the same amount of cesium in the absence of potassium. For example, Examples 3 and 7 relate to catalysts having an identical atomic ratio of cesium to silver (0.05 atoms/100 atoms Ag), but differing potassium contents, the atomic ratio of potassium in Example 3 being 0.001 atoms K/100 atoms Ag and the corresponding ratio in Example 7 being 0.05. The efficiency achieved in Example 3 was 76.4% and that of Example 7 was 75.9%. Thus, the increased potassium content in Example 7 resulted in a decrease in catalyst efficiency. Similarly, Examples 1 and 4 relate to catalysts having an identical atomic ratio of cesium to silver, with the catalyst of Example 1 containing an amount of potassium one order of magnitude greater than the catalyst of Example 4. Yet, the efficiencies reported for both catalysts are essentially the same, 76.7% and 76.6% for Examples 1 and 4, respectively.

U.S. Pat. No. 4,039,561 discloses a catalyst for preparing ethylene oxide containing silver, tin, antimony, thallium, potassium, cesium and oxygen in specified atomic ratios. Mixtures of cesium and potassium are not disclosed to be desirable combinations. Indeed, Table I of the patent discloses a silver-cesium-potassium combination which is designated as a "control" example not in accord with the disclosed invention and which achieved a selectivity of 73.0%, a value markedly lower than the selectivities achieved in the 45 Examples listed in Tables 2 and 3. Moreover, the efficiencies provided in Tables 2 and 3 for the various catalysts fail to demonstrate the existence of any synergistic combination of cesium and potassium among the numerous combination of elements which were employed in the catalysts. It is also note-worthy that the aforesaid U.S. Pat. No. 4,039,561 claims the priority of a Japanese application filed in 1973, and that subsequent to such filing the same applicant filed Japanese Application Publication No. 25703/77 which discloses a catalyst for ethylene oxide manufacture comprised of the same metallic elements disclosed in the U.S. patent with exception of cesium and potassium. The efficiencies disclosed in the examples of the latter Japanese Application are similar to those shown in the U.S. patent. The effect of cesium and potassium in the catalyst composition disclosed in the U.S. patent is therefore presumably insignificant.

Belgium Patent No. 854,904 discloses silver catalysts containing various mixtures of sodium and cesium. U.K. Patent Application No. GB 2,002252A discloses, in Table 2, supported silver catalysts containing various mixtures of cesium and thallium, some of which additionally contain potassium or antimony. U.S. Pat. No. 4,007,135 broadly discloses (in column 2, lines 25-30) silver catalysts for alkylene oxide production containing silver "together with a promoting amount of at least one promoter selected from lithium, potassium, sodium, rubidium, cesium, copper, gold, magnesium, zinc, cadmium, strontium, calcium, niobium, tantalum, molybdenum, tungsten, chromium, vanadium and barium . . . ". European Patent Publication No. 0003642 discloses, in Table 3, silver-containing catalysts which include mixtures of potassium and cesium, and a catalyst containing sodium and cesium. The above publication do not indicate synergistic interaction of cesium with other alkali metals.

Belgium Patent No. 867,045 discloses supported silver catalysts containing what is referred to as an effective proportion of lithium and a substantially lesser amount of alkali metal selected from among cesium, rubidium and/or potassium. Table I of the patent discloses three catalysts all of which contain cesium, sodium, potassium and lithium, the lithium concentration being at least one order of magnitude greater than the concentration of cesium or potassium. Referring to Table I, the catalysts L1, L2 and L3 have markedly different concentrations of cesium, potassium and sodium, but are shown in Table II to provide substantially similar selectivities. There is no indication of a synergistic interaction of cesium with either potassium or sodium in the silver catalysts disclosed.

Belgium Patent No. 867,185 discloses supported silver catalysts for ethylene oxide production containing a specified amount of potassium and at least one other alkali metal selected from rubidium and cesium. Table I discloses the composition of 14 potassium-containing catalysts, two of which contain potassium in combination with cesium (catalysts G and H). The selectivities of catalysts G and H are shown to be identical at a pressure of 1.03 bars, but differ slightly at the higher pressure of 16.55 bars. No silver-potassium-cesium synergism can be discerned from the data.

This invention distinguishes over the prior art in the fact that the silver catalyst employed in manufacturing ethylene oxide utilizes at least two alkali metals (excluding francium), one of which is cesium, each of the alkali metals being present in an amount such that the combination thereof in relation to the amount of silver in the catalyst provides a synergy in terms of ethylene oxide selectivity and a selectivity which is greater than has been contemplated or disclosed by any prior art.

DETAILED DESCRIPTION OF THE INVENTION

The process and the catalysts of the invention are characterized by a combination of (a) cesium and (b) at least one other alkali metal selected from the group consisting of lithium, sodium, potassium and rubidium so as to achieve a synergistic result, i.e., an efficiency greater than the greater value obtainable under common conditions from respective catalysts which are the same as said catalyst except that instead of containing both (a) and (b), one contains the respective amount of (a), and the other contains the respective amount of (b). Catalysts in accord with the invention are comprised of silver, cesium and at least one other alkali metal (excluding francium) deposited onto the surface of a porous support, the particular mixture of silver and alkali metals being correlated to produce a synergistic result.

The invention as hereinafter described defines the binary alkali metal combinations of cesium-lithium, cesium-sodium, cesium-potassium and cesium-rubidium, which in combination with silver provide a synergistic result for a particular catalyst carrier and catalyst preparation. The catalysts of the invention are not, however, restricted to binary combinations of alkali metal. Other alkali metals may advantageously be added to any of the aforementioned synergistic binary combinations for the purpose of raising or lowering the catalyst operating temperature improving the initial catalyst activity during the start-up period and/or improving the aging characteristics or the catalyst over prolonged periods of operation. In some instances, the addition of a third or even a fourth alkali metal to an otherwise synergistic binary combination will effect a further increase in catalyst efficiency.

The mathematical relationships from which are derived the synergistic binary alkali metal combinations of the invention are set forth below and described, for purposes of illustration, in terms of a cesium-potassium combination. Binary combinations of cesium with any of the other alkali metals in accordance with the invention are readily determined by an analogous procedure wherein the particular alkali metal of interest is substituted for potassium in the procedure described below.

The relationship of cesium, potassium and silver to achieve a synergistic result as herein defined is characterized with the aid of a mathematical equation, or model, which correlates efficiency as a function of weight percent silver, weight percent cesium and weight percent potassium deposited on the catalyst support. Thus, synergism with mixtures of cesium and potassium can be obtained at any concentration of silver in the finished catalyst.

The general form of the mathematical equation, hereinafter referred to as the "Efficiency Model", defines efficiency (or selectivity) as a function of weight percents (wt. %) of silver, cesium and potassium deposited on the catalyst support as follows:

$$\text{Efficiency, \%} = b_0 + b_1(BG) + b_2(BCs) + b_3(BK) + b_4(BG)^2 + b_5(BCs)^2 + b_6(BK)^2 + b_7(BG \times BCs) + b_8(BG \times BK) + b_9(BCs \times BK)$$

where: $b_0$, $b_1$, $b_2$, $b_3$, $b_4$, $b_5$, $b_6$, $b_7$, $b_8$ and $b_9$ are the respective coefficients for each term of the Efficiency Model, and comprise a set of constants determined for a particular catalyst carrier and a particular method of catalyst preparation following a designed set of experiments as hereinafter described. The value of some of these coefficients may be zero.

$BG = (\text{wt. \% Ag} - \overline{\text{wt. \% Ag}})$;

where, $\overline{\text{wt. \% Ag}}$ = average value of wt. % Ag used in the designed set of experiments.

$BCs = (\text{wt. \% Cs} - \overline{\text{wt. \% Cs}})$;

$\overline{\text{wt. \% Cs}}$ = average value of wt. % Cs used in the designated set of experiments.

$BK = (\text{wt. \% K} - \overline{\text{wt. \% K}})$;

where, $\overline{\text{wt. \% K}}$ = average value of wt. % K used in the designed set of experiments.

The designed set of experiments is most conveniently planned in the format of a Composite Design in three independent variables as described by O. L. Davies, "The Design and Analysis Of Industrial Experiments", Hafner Publishing Company, 1960, P. 532-535. For this purpose, the three independent variables are the weight percents of silver, cesium and potassium, respectively. The ranges of each variable are chosen so that selectivity and activity of all catalysts in the designed set of experiments can be measured under the desired test conditions. It is therefore desirable to first conduct a few preliminary range finding experiments to determine the appropriate ranges of cesium and potassium for this purpose. Zero percent cesium and/or potassium is a convenient lower limit for use in the Composite Design. The upper concentration limit of cesium and potassium can be readily determined by a series of experiments with catalysts containing successively larger amounts of either cesium or potassium as follows: An initial catalyst is prepared (using a preparation procedure, if desired, such as hereinafter disclosed in the Examples) containing a small amount (on the order of about 0.001 percent by weight) of either cesium or potassium with a fixed amount, say 7 percent by weight, of silver, and its selectivity then determined for the production of ethylene oxide at the desired test conditions. This experiment is then repeated with a catalyst containing double the amount (0.002 percent by weight) of the alkali metal and the experiment thus repeated in a series of experiments wherein each succeeding experiment uses a catalyst containing double the alkali metal content of the catalyst of the previous experiment, until the measured selectivity of the last catalyst tested is less than that of the initial catalyst. The upper limit of cesium or potassium concentration is thus defined for the Composite Design.

The above-described interative procedure may be advantageously altered so as to more quickly determine the upper limit of concentration in the event it is observed that a two-fold increase in the alkali metal content of the catalyst does not produce a significant change in catalyst selectivity. This is particularly likely to occur, for example, with catalysts containing lithium or sodium (depending upon the particular carrier and preparation procedure employed) in contrast to catalysts containing other alkali metals where, as a general rule, the efficiency response is more sensitive to increasing alkali concentration. Accordingly, in the event the catalyst efficiency is virtually unchanged when the alkali content of the catalyst has been doubled, a ten-fold increase in alkali content should be employed in the above-described iteration until the measured efficiency of the last catalyst is less than that of the initial catalyst. Thereafter it may be desirable to repeat the last iterative step using a lower level of alkali, such as, a three or five-fold increase of alkali metal content, in order to more accurately determine the upper limit of alkali metal concentration for the Composite Design.

The range of silver concentration in the Composite Design may typically be 6–16 weight percent, giving an average value of silver wt. % $\overline{Ag}$ of 11 weight percent. Similarly, the ranges of cesium and potassium concentrations are typically from 0.0 to 0.02 weight percent. For rubidium, the range is also typically from 0.0 to 0.02 weight percent, while for lithium and sodium, the ranges are typically 0.0 to 0.1 weight percent. For some carriers, the upper concentration limit of cesium and/or potassium may be 5 to 10 times greater. This is particularly likely to occur for carriers which contain exchangeable cations.

Table 11.5 on page 533 of the aforementioned Davies Publication depicts a three-variable Composite Design scaled in units of $-\alpha$, $-1$, 0, $+1$ and $+\alpha$ where $-1$ represents a "low level" of the respective variable; $+1$ represents a "high level" of such variable; 0 represents the average level of the variable; $-\alpha$ represents a level which is somewhat lower in value than that which is represented by $-1$; and $+\alpha$ represents a level which is somewhat higher than that represented by $+1$. The particular choice of $-\alpha$ and $+\alpha$ is not critical. However, Table 11.6 on page 534 of the Davies Publication suggests values of $-\alpha$ and $+\alpha$ which are particularly useful for a Composite Design in accordance with the present invention. The designed set of experiments is thus typically comprised of 16 to 20 experiments wherein catalysts of varying concentrations of silver, cesium, and potassium are tested. Thus, for example, a preferred Composite Design in which the weight percent silver ranges from 7.0 to 15.0%; the weight percent cesium ranges from 0.0 to 0.02%; and the weight percent potassium ranges from 0.0 to 0.01% is as follows:

| Wt. % Silver | Wt. % Cesium | Wt. % Potassium |
| --- | --- | --- |
| 9 | 0.005 | 0.002 |
| 13 | 0.005 | 0.002 |
| 9 | 0.015 | 0.002 |
| 13 | 0.015 | 0.002 |
| 9 | 0.005 | 0.008 |

-continued

| Wt. % Silver | Wt. % Cesium | Wt. % Potassium |
|---|---|---|
| 13 | 0.005 | 0.008 |
| 9 | 0.015 | 0.008 |
| 13 | 0.015 | 0.008 |
| 11 | 0.010 | 0.005 |
| 11 | 0.010 | 0.005 |
| 7 | 0.010 | 0.005 |
| 15 | 0.010 | 0.005 |
| 11 | 0.0 | 0.005 |
| 11 | 0.020 | 0.005 |
| 11 | 0.010 | 0.0 |
| 11 | 0.010 | 0.010 |

The catalysts of the designed set of experiments are tested by means well known in the art for measuring their selectivity and activity. A convenient measure of activity, i.e., the degree of conversion of reactant to product per unit time, is the temperature required to obtain either a fixed ethylene oxide production or to achieve a chosen level of mole percent ethylene (or oxygen) conversion. Thus, a mathematical equation for catalyst temperature (Temperature Model) can be developed in a manner similar to the Efficiency Model. That is, for each catalyst there is obtained two responses (selectivity and temperature) which are related to the three controlled variables (weight percents of silver, cesium, and potassium). The relationship between each response and the controlled variables is obtained by fitting these data to equations, or mathematical models, by the method of least squares as described in Chapter 8 of "Statistical Methods in Research and Production", O. L. Davies and P. L. Goldsmith, Longman Croup, Ltd., London, 4th Ed., 1976. In practice, the fitting of mathematical models to such data is routinely done with the aid of a digital computer as described in "Applied Regression Analysis", N. R. Draper and H. Smith, John Wiley and Sons, Inc., 1966. The resulting models (the Efficiency Model and the Temperature Model) describe the relationship between the responses and the controlled variables.

It is well known in the art that the number of experiments required to establish mathematical relationships among several variables is dependent upon the reproducibility of the data. Thus, for a Composite Design containing approximately 16 experiments it may occasionally be necessary to repeat all or part of the set of designed experiments in order to firmly establish the relationship between efficiency and weight percents of silver, cesium and potassium to an acceptable level of statistical confidence. In practice, it has been found that for a designed set of about 16 experiments wherein the weight percent of silver is varied from about 7% to about 15%, one complete replication of the designed experiments is usually sufficient to establish this relationship provided that the standard deviation of a single experimental test result is no greater than about 0.7% efficiency units. During the course of experimentation, data other than from the designed set of experiments may be acquired which is useful for developing the model as described above. For example, data acquired from the aforementioned preliminary range finding experiments as well as any additional experimental data which is available with regard to the particular catalyst carrier and method of preparation of interest is desirably included with that derived from the Composite Design, and the equations thus fitted to the data. Consequently, as a practical matter, data from about 30 to 60 experiments may be available for developing the Efficiency and Temperature Models.

The general form of the mathematical equation, hereinafter referred as the "Temperature Model" defines temperature as a function of weight percents of silver, cesium and potassium deposited on the catalyst support as follows:

$$\text{Temp., }°C. = a_0 + a_1(BG) + a_2(BCs) + a_3(BK) +$$
$$a_4(BG)^2 + a_5(BCs)^2 + a_6(BK)^2 +$$
$$a_7(BCs \times BG) + a_8(BG \times BK) + a_9(BCs \times BK)$$

where; $a_0$, $a_1$, $a_2$, $a_3$, $a_4$, $a_5$, $a_6$, $a_7$, $a_8$ and $a_9$ are the respective coefficients for each term in the Temperature Model which comprise a set of constants determined for a particular carrier and a particular method of catalyst preparation following the designed set of experiments as described above. The value of some of these coefficients may be zero. BG, BCs, and BK are as defined above.

Figure 1:
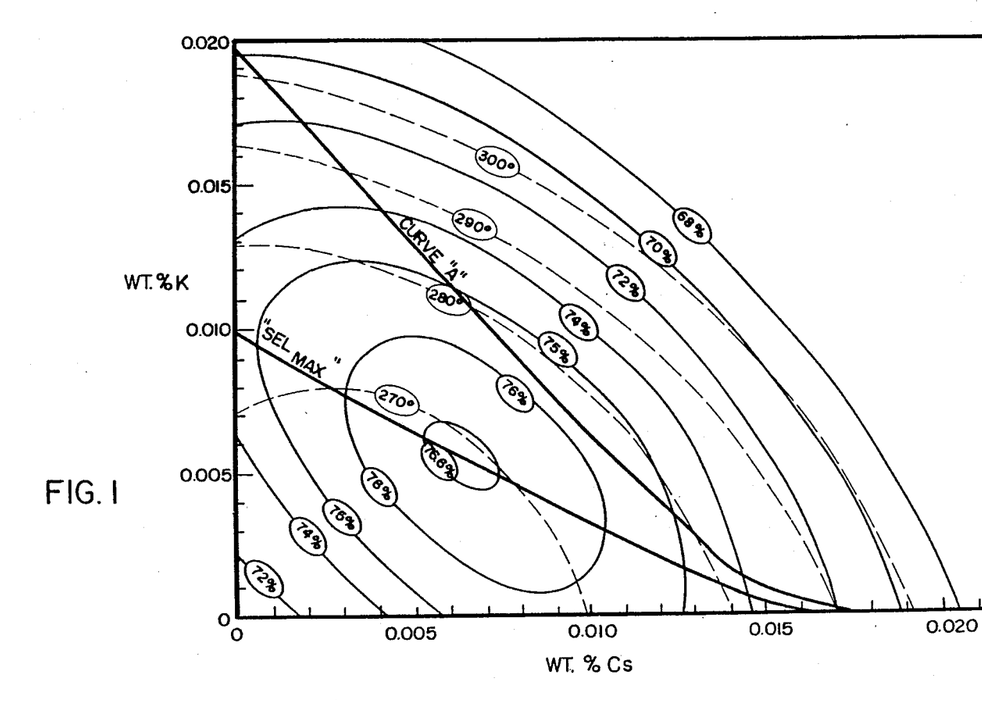
Figure 2:
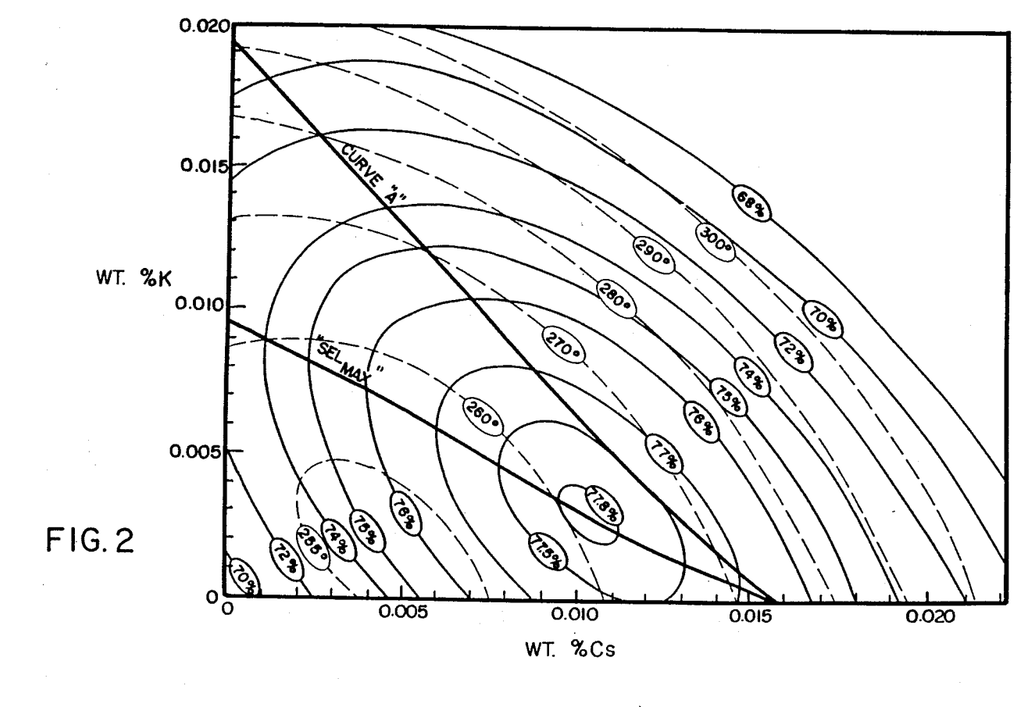

The most convenient use of the Efficiency and Temperature Models for defining the area of synergism for any selected weight percent of silver in the catalyst is to depict efficiency and temperature responses in a graphical form, commonly referred to as contour maps, as described in Chapter 11 of the aforementioned "Design and Analysis of Industrial Experiments". Thus, FIGS. 1 and 2 depict the contour maps of efficiency and temperature for a selected carrier and catalyst preparation procedure at 7 and 13 weight percent silver, respectively. The contour maps were derived from a designed set of experiments in which the percent silver ranged from 5.88 to 16.05%; the percent cesium ranged from 0.00 to 0.019%; and the percent potassium ranged from 0.00 to 0.021%. Table I below summarizes the experimental data which was available for the selected carrier and catalyst preparation procedure and from which the contour maps were derived. The experiments were conducted in two different test reactors in accordance with the standard test procedure hereinafter described under the heading "Catalyst Comparisons". Two similar, but slightly different, carriers were used in the experiments. Table I represents the experimental data on a common basis, namely, the data were adjusted to compensate for observed differences between the reactors and catalyst carriers employed.

TABLE I

| wt % Ag | wt % Cs | wt % K | Temp. (°C.) | Efficiency (%) |
|---|---|---|---|---|
| 11.14 | 0.00477 | 0.00158 | 256.0 | 73.9 |
| 10.53 | 0.00897 | 0.0 | 256.4 | 77.5 |
| 11.14 | 0.00479 | 0.0 | 256.0 | 72.9 |
| 11.01 | 0.00941 | 0.00312 | 256.0 | 77.4 |
| 11.21 | 0.00240 | 0.00080 | 258.0 | 70.7 |
| 10.92 | 0.01865 | 0.0 | 282.2 | 74.3 |
| 11.04 | 0.00941 | 0.0 | 257.2 | 76.3 |
| 11.04 | 0.00941 | 0.0 | 255.0 | 76.3 |
| 11.09 | 0.01421 | 0.00412 | 270.7 | 75.7 |
| 10.41 | 0.0 | 0.0 | 263.0 | 68.5 |
| 10.41 | 0.0 | 0.0 | 265.0 | 68.4 |
| 11.16 | 0.01909 | 0.00633 | 292.6 | 72.0 |
| 10.94 | 0.01403 | 0.0 | 267.0 | 76.7 |
| 10.70 | 0.01128 | 0.00379 | 262.0 | 77.5 |
| 9.08 | 0.01900 | 0.00315 | 293.0 | 71.8 |
| 9.31 | 0.00968 | 0.00645 | 269.9 | 76.6 |
| 13.17 | 0.00617 | 0.00102 | 254.9 | 74.2 |
| 9.10 | 0.00323 | 0.00214 | 260.0 | 72.7 |
| 13.14 | 0.00915 | 0.00613 | 259.1 | 77.5 |
| 11.11 | 0.00950 | 0.00315 | 259.6 | 77.6 |
| 11.31 | 0.01208 | 0.0 | 260.3 | 77.4 |
| 11.05 | 0.00236 | 0.00078 | 260.4 | 70.1 |
| 12.72 | 0.00311 | 0.00207 | 255.8 | 71.6 |

TABLE I-continued

| wt % Ag | wt % Cs | wt % K | Temp. (°C.) | Efficiency (%) |
|---|---|---|---|---|
| 16.05 | 0.00941 | 0.00313 | 263.0 | 77.7 |
| 5.88 | 0.00924 | 0.00306 | 269.1 | 76.8 |
| 11.04 | 0.01421 | 0.00157 | 268.9 | 76.7 |
| 10.89 | 0.00462 | 0.00450 | 256.4 | 75.4 |
| 10.80 | 0.0 | 0.00613 | 260.5 | 69.9 |
| 8.93 | 0.00630 | 0.00105 | 260.4 | 74.4 |
| 15.51 | 0.01288 | 0.0 | 266.4 | 77.2 |
| 6.03 | 0.01341 | 0.0 | 280.3 | 73.7 |
| 13.11 | 0.00897 | 0.00810 | 266.2 | 77.1 |
| 16.00 | 0.00888 | 0.00800 | 264.3 | 77.8 |
| 10.93 | 0.0 | 0.01230 | 263.6 | 73.3 |
| 12.95 | 0.01562 | 0.00469 | 277.1 | 76.0 |
| 13.12 | 0.01313 | 0.00386 | 268.1 | 77.0 |
| 12.85 | 0.00150 | 0.0 | 264.4 | 68.2 |
| 13.12 | 0.01047 | 0.00297 | 257.3 | 78.3 |
| 13.26 | 0.01784 | 0.00540 | 282.3 | 74.5 |
| 12.91 | 0.01384 | 0.00407 | 269.4 | 77.0 |
| 12.91 | 0.01384 | 0.00407 | 269.8 | 77.2 |
| 12.91 | 0.01038 | 0.00295 | 257.0 | 78.3 |
| 12.91 | 0.01038 | 0.00295 | 257.2 | 78.6 |
| 13.00 | 0.00150 | 0.02100 | 299.0 | 67.0 |
| 13.00 | 0.01038 | 0.01500 | 290.7 | 72.2 |
| 6.88 | 0.00150 | 0.01470 | 288.6 | 73.7 |
| 7.14 | 0.01056 | 0.01220 | 289.2 | 72.3 |
| 7.06 | 0.00594 | 0.01010 | 280.4 | 75.2 |
| .8.00 | 0.00727 | 0.00192 | 263.3 | 75.7 |
| 8.00 | 0.01153 | 0.00330 | 274.4 | 76.9 |
| 8.15 | 0.01171 | 0.00339 | 272.7 | 77.6 |
| 8.30 | 0.00749 | 0.00199 | 262.2 | 76.5 |
| 8.03 | 0.00150 | 0.0 | 268.0 | 69.0 |
| 7.00 | 0.01056 | 0.0 | 264.0 | 75.5 |
| 7.00 | 0.01056 | 0.00400 | 271.0 | 76.2 |

The specific Efficiency and Temperature Models derived from the above data by the aforementioned method of least square are as follows:

Efficiency, % = 77.19 + 0.196(BG) + 133.4(BCs)
+ 120.5(BK) − 63787.0 (BCs)$^2$
− 47229.0 (BK)$^2$ + 52.1 (BG × BCs)
− 60823.0 (BCs × BK); and Temperature, °C. = 259.44 − 1.279(BG) + 1555.8(BCs)
+ 794.1(BK) + 0.3466(BG)$^2$
+ 168544.0(BCs)$^2$ + 147856.0(BK)$^2$
+ 132807.0(BCs × BK)

where:

BG = (wt. % Ag − 11.0)

BCs = (wt. % Cs − 0.01)

BK = (wt. % K − 0.003)

BRIEF DESCRIPTION OF THE DRAWINGS

FIGS. 1 and 2 show contour lines of constant efficiency and temperature in potassium-cesium concentration space. The darker lines represent selectivity contours with selectivity values being indicated for each line. The lighter, broken lines represent temperature contours with temperatures indicated in degrees centigrade. The efficiency and temperature for points in between the designated contour lines can be interpolated. The maximum selectivity achievable for any combination of cesium and potassium as a function of cesium concentration is indicated by the curve labelled Sel$_{Max}$. This curve represents the maximum synergism achievable for any given level of cesium. The synergism curve (designated "A" in FIGS. 1 and 2) separates the region of synergism, as herein defined, and regions of additive and antagonistic effects. Additive effects occur when the efficiency obtained with a combination of cesium and potassium is a weighted average of the efficiencies obtainable under common conditions from respective catalysts which are the same as the catalyst containing said combination except that instead of containing both potassium and cesium, one contains the respective amount of cesium, and the other contains the respective amount of potassium. Antagonistic effects occur when the efficiency obtainable with a mixture of cesium and potassium is less than the efficiencies obtainable with corresponding catalysts which contain the respective amount of cesium, and the respective amount of potassium, individually, as described above. The area bound by ordinate, the abscissa and the synergism curve (curve "A") defines the area of synergism in accordance with the present invention. The area to the right of the synergism curve "A", represents the area of additive and antagonistic effects as described above, and thus defines mixtures not in accord with the present invention. For any given contour map the preferred combinations of cesium and potassium are those which produce selectivities on or about the Sel$_{Max}$ curve. However, in general, preferred mixtures are those wherein cesium and potassium are present in a weight ratio of from about 100:1 to 1:100 depending upon the particular catalyst carrier and preparation procedure of choice. For mixtures of cesium and lithium, or cesium and sodium, preferred mixtures are usually those wherein the alkali metals are present in a weight ratio of from about 1000:1 to 1:1000.

Referring to FIG. 1, a catalyst containing for example, 0.003% Cs and 0% K has an efficiency of about 73%. The addition of approximately 0.008% K to this catalyst results in an increase in efficiency to about 6.0%, the maximum selectivity at this level of cesium (i.e., the value on the Sel$_{MAX}$ curve). Further additions of potassium up to about 0.016% K (i.e., the value on curve "A") would yield efficiencies equal to or greater than those obtainable with the given amount (0.003%) of cesium alone (i.e., no alkali metal other than cesium being present); potassium additions beyond 0.016% K result in efficiencies lower than those obtainable with 0.003% of cesium alone, i.e., in the region of either additive or antagonistic effects. Yet, such amount of potassium which causes such antagonistic effects can still yield a catalyst with reasonably desirable selectivity and activity for a given mode of operation.

The region of synergism varies with the silver content of the catalyst as described by the Efficiency Model. FIG. 2 illustrates the region of synergism at 13% silver. The Sel$_{Max}$ curve and synergism curve (curve "A") of FIG. 2 are as previously defined with reference to FIG. 1. Comparison of FIGS. 1 and 2 show that the efficiency contour lines are similar but are displaced with respect to the cesium and potassium axes. For example, the 76% efficiency contour line in FIG. 1 envelops an area which is smaller than the area covered by the corresponding contour line in FIG. 2. Further, the maximum value of selectivity obtainable at 7 weight percent silver, i.e., the maximum along the Sel$_{Max}$ line, is slightly above 76% (FIG. 1) while the corresponding maximum for 13 weight percent silver is slightly above 77.8% (FIG. 2).

The Efficiency Model and the Temperature Model which are developed are specific to a particular method of catalyst preparation, a particular carrier and a particular binary alkali metal combination. Variations in either the method of preparation or the carrier or the particular binary combination ma change the coefficients of the Models, and hence, the shape of the contour maps derived therefrom. Thus, the curves "A" and $Sel_{Max}$ may comprise straight lines or curves, and may intercept one or both axes (viz., the cesium axis and that of the other alkali metal in the binary combination). For example, in FIGS. 1 and 2, curve "A" and $Sel_{Max}$ intercept both axes, and intercept the cesium axis at an angle greater than 90°. However, for a different carrier, a different method of preparation or a different binary alkali metal combination with cesium, the resultant curves "A" and $Sel_{Max}$ may intercept the cesium axis at an angle less than 90°, or may be parallel to one of the axes. The coefficients of the Model and the resultant contour maps can be readily determined for any of the aforementioned variations using the designed set of experiments as described above.

The concentration of silver in the finished catalyst may vary from about 2 to 20 weight percent, the preferred range being from about 6% to about 16% by weight of silver. Lower silver concentrations are preferred from an economic standpoint. However, the optimum silver concentration for any particular catalyst will be dependent upon economic factors as well as performance characteristics, such as, catalyst efficiency, rate of catalyst aging and reaction temperature.

CATALYST PREPARATION

A variety of procedures may be employed for preparing catalysts containing combinations of cesium and one or more other alkali metals (excluding francium) in accordance with the present invention. The preferred procedure comprises: (1) impregnating a porous catalyst carrier with a solution comprising a solvent or solubilizing agent, silver salt in an amount sufficient to deposit the desired weight of silver upon the carrier, and salts of (a) cesium and (b) at least one other alkali metal selected from the group consisting of lithium, sodium, potassium and rubidium sufficient to deposit respective amounts of (a) and (b) on the support such that the efficiency of ethylene oxide manufacture of the finished catalyst is increased to a value greater than the efficiencies obtainable under common conditions from respective catalysts which are the same as said catalyst except that instead of containing both (a) and (b), one contains the respective amount of (a), and the other contains the respective amount of (b); and thereafter (2) treating the impregnated support to convert at least a fraction of the silver salt to silver metal and effect deposition of silver, (a) and (b), respectively, on the support surface. Silver and alkali metal deposition are generally accomplished by heating the carrier at elevated temperatures to evaporate the liquid within the support and effect deposition of the silver and alkali metal onto the interior and exterior carrier surfaces. Alternatively, a coating of silver and alkali metals may be formed on the carrier from an emulsion or slurry containing the same followed by heating the carrier as described above. Impregnation of the carrier is generally the preferred technique for silver deposition because it utilizes silver more efficiently than coating procedures, the latter being generally unable to effect substantial silver deposition onto the interior surfaces of the carrier. In addition, coated catalysts are more susceptible to silver loss by mechanical abrasion.

The sequence of impregnating or depositing the surfaces of the carrier with silver and alkali metals is optional. Thus, impregnation and deposition of silver and alkali metals may be effected coincidentally or sequentially, i.e., the alkali metals may be deposited prior to, during, or subsequent to silver addition to the carrier. The alkali metals may be deposited together or sequentially. For example, cesium may be deposited first followed by the coincidental or sequential deposition of silver and the other alkali metal(s), or such other alkali metal(s) may be deposited first followed by coincidental or sequential deposition of silver and cesium.

Impregnation of the catalyst carrier is effected using one or more solutions containing silver and alkali metal compounds in accordance with well-known procedures for coincidental or sequential depositions. For coincidental deposition, following impregnation the impregnated carrier is heat or chemically treated to reduce the silver compound to silver metal and deposit the alkali metals onto the catalyst surfaces. For sequential deposition, the carrier is initially impregnated with silver or alkali metal (depending upon the sequence employed) and then heat or chemically treated as described above. This is followed by a second impregnation step and a corresponding heat or chemical treatment to produce the finished catalyst containing silver and alkali metals.

The silver solution used to impregnate the carrier is comprised of a silver salt or compound in a solvent or complexing/solubilizing agent such as the silver solutions disclosed in the art. The particular silver salt or compound employed is not critical and may be chosen, for example, from among silver nitrate, silver oxide or silver carboxylates, such as, silver acetate, oxalate, citrate, phthalate, lactate, propionate, butyrate and higher fatty acid salts.

A wide variety of solvents or complexing/solubilizing agents may be employed to solubilize silver to the desired concentration in the impregnating medium. Among those disclosed in the art as being suitable for this purpose are lactic acid (U.S. Pat. Nos. 2,477,435 to Aries; and 3,501,417 to DeMaio); ammonia (U.S. Pat. No. 2,463,228 to West et al); alcohols, such as ethylene glycol (U.S. Pat. Nos. 2,825,701 to Endler et al; and 3,563,914 to Wattimena); and amines and aqueous mixtures of amines (U.S. Pat. Nos. 2,459,896 to Schwarz; 3,563,914 to Wattimena; 3,702,259 to Nielsen; and 4,097,414 to Cavitt).

Suitable alkali metal salts include all those soluble in the particular solvent or solubilizing agent employed. Accordingly, inorganic and organic salts of alkali metals, such as, nitrates, halides, hydroxides, sulfates and carboxylates ma be used. When coincidentally deposited with silver, the alkali metal salt employed is preferably one which does not react with silver salt in solution in order to avoid premature silver precipitation from same. Thus, for example alkali metal halides are preferably not used in lactic acid solution because they react with silver ions present therein.

Following impregnation of the catalyst carrier with silver and alkali metal salts, the impregnated carrier particles are separated from any remaining non-absorbed solution or slurry. This is conveniently accomplished by draining the excess impregnating medium or alternatively by using separation techniques, such as, filtration or centrifugation. The impregnated carrier is then generally heat treated (e g., roasted) to effect decomposition and reduction of the silver metal salt to metallic silver and the deposition of alkali metal ion. Such roasting may be carried out at a temperature of from about 100° C. to 900° C., preferably from 200° to 700° C., for a period of time sufficient to convert substantially all of the silver salt to silver metal. In general, the higher the temperature, the shorter the required reduction period. For example, at a temperature of from about 400° C. to 900° C., reduction may be accomplished in about 1 to 5 minutes. Although a wide range of heating periods have been suggested in the art to thermally treat the impregnated support, (e.g., U.S. Pat. No. 3,563,914 suggests heating for less than 300 seconds to dry but not roast reduce the catalyst., U.S. Pat. No. 3,702,259 discloses heating from 2 to 8 hours at a temperature of from 100° C. to 375° C. to reduce the silver salt in the catalyst; and U.S. Pat. No. 3,962,136 suggests ½ to 8 hours for the same temperature range) it is only important that the reduction time be correlated with temperature such that substantially complete reduction of the silver salt to metal is accomplished. A continuous or step-wise heating program may be used for this purpose.

Heat treatment is preferably carried out in air, but a nitrogen or carbon dioxide atmosphere may also be employed. The equipment used for such heat treatment may use a static or flowing atmosphere of such gases to effect reduction.

The particle size of silver metal deposited upon the carrier is a function of the catalyst preparation procedure employed. Thus, the particular choice of solvent and/or complexing agent, silver salt, heat treatment conditions and catalyst carrier may affect, to varying degrees, the size of the resulting silver particle. For carriers of general interest for the production of ethylene oxide, a distribution of silver particle sizes in the range of 0.05 to 2.0 microns is typically obtained. However, the role of particle size of the silver catalyst upon the effectiveness of the catalyst in making ethylene oxide is not clearly understood. In view of the fact that the silver particles are known to migrate on the surface of the catalyst when used in the catalytic reaction resulting in a marked change in their size and shape, silver particle size may not be a significant factor in affecting catalytic performance.

CARRIER SELECTION

The catalyst carrier employed in practicing the invention may be selected from conventional, porous, refractory materials which are essentially inert to ethylene, ethylene oxide and other reactants and products at reaction conditions. These materials are generally labelled as "macroporous" and consist of porous materials having surface areas less than 10 $m^2/g$ (square meters per gm of carrier) and preferably less than 1 $m^2/g$. The surface area is measured by the conventional B.E.T. method described by Brunauer, S., Emmet, P., and Teller, E., in J. Am. Chem. Soc. Vol. 60, pp309–16, (1938). They are further characterized by pore volumes ranging from about 0.15–0.8 cc/g, preferably from about 0.2–0.6 cc/g. Pore volumes may be measured by conventional mercury porosimetry or water absorption techniques. Median pore diameters for the above-described carriers range from about 0.01 to 100 microns, a more preferred range being from about 0.5 to 50 microns.

The carrier should preferably not contain ions which are exchangeable with the alkali metals supplied to the catalyst, either in the preparation or use of the catalyst, so as to upset the amount of alkali metal which provides the desired synergism. If the carrier contains such ion, the ion should be removed by standard chemical techniques such as leaching. Moreover, if the carrier contains an amount of alkali metal, which is transferable to the silver whereby the synergistic combination is upset, then the carrier should be treated to remove such excess alkali metal or the amount of alkali metal supplied to the catalyst should be less than the synergistic amount, allowing the transferred alkali metal to effect the desired synergistic amounts.

The chemical composition of the carrier is not narrowly critical. Carriers may be composed, for example, of alpha-alumina, silicon carbide, silicon dioxide, zirconia, magnesia and various clays. In general, alpha-alumina based materials are preferred. These alpha-alumina based materials may be of very high purity, i.e., 98+ wt. % alpha-alumina, the remaining components being silica, alkali metal oxides (e.g., sodium oxide) and trace amounts of other metal and non-metal impurities; or they may be of lower purity, i.e., about 80 wt. % alpha-alumina, the balance being a mixture of silicon dioxide, various alkali oxides, alkaline earth oxides, iron oxide, and other metal and non-metal oxides. The lower purity carriers are formulated so as to be inert under catalyst preparation and reaction conditions. A wide variety of such carriers are commercially available. The carriers may be in the form of pellets, extruded particles spheres, rings and the like. The size of the carriers may vary from about 1/16" to ½". The carrier size is chosen to be consistent with the type of reactor employed. In general, for fixed bed reactor applications, sizes in the range of ⅛" to ⅜" have been found to be most suitable in the typical tubular reactor used in commercial operations.

ETHYLENE OXIDE PRODUCTION

The silver catalysts of the invention are particularly suitable for use in the production of ethylene oxide by the vapor phase oxidation of ethylene with molecular oxygen. The reaction conditions for carrying out the oxidation reaction are well-known and extensively described in the prior art. This applies to reaction conditions, such as, temperature, pressure, residence time, concentration of reactants, diluents (e.g., nitrogen. methane and $CO_2$), inhibitors (e.g., ethylene dichloride) and the like. In addition, the desirability of recycling unreacted feed, or employing a single-pass system, or using successive reactions to increase ethylene conversion by employing reactors in series arrangement can be readily determined by those skilled in the art. The particular mode of operation selected will usually be dictated by process economics.

Generally, the process is carried out by continuously introducing a feed stream containing ethylene and oxygen to a catalyst-containing reactor at a temperature of from about 200° to 300° C., and a pressure which may vary from one atmosphere to about 30 atmospheres depending upon the mass velocity and productivity desired. Residence times in large-scale reactors are generally on the order of about 1–5 seconds. Oxygen may be supplied to the reaction in an oxygen-containing stream, such as, air or as commercial oxygen. The resulting ethylene oxide is separated and recovered from the reaction products using conventional methods.

CATALYST COMPARISONS

The catalysts cited in the Tables below were all evaluated for comparison purposes under standard test conditions using backmixed, bottom-agitated "Magnedrive" autoclaves as described in FIG. 2 of the paper by J. M. Berty entitled "Reactor for Vapor Phase-Catalytic Studies", in Chemical Engineering Progress, Vol 70, No. 5, pages 78–84, 1974. The reactor was operated at 1.0 mole % ethylene oxide in the outlet gas under the following standard inlet conditions:

| Component | Mole % |
|---|---|
| Oxygen | 6.0 |
| Ethylene | 8.0 |
| Ethane | 0.50 |
| Carbon Dioxide | 6.5 |
| Nitrogen | Balance of Gas |
| Parts per million Ethylene Chloride | = 7.5 |

The pressure was maintained constant at 275 psig and the total outlet flow maintained at 22.6 SCFH.[1] The outlet ethylene oxide concentration was maintained at 1.0% by adjusting the reaction temperature. Thus, temperature (° C.) and catalyst efficiency are obtained as the responses describing the catalyst performance.
(1) SCFH refers to cubic feet per hour at standard temperature and pressure, namely, 0° C. and one atmosphere.

A typical catalyst test procedure is comprised of the following steps:

1. 80 cc of catalyst is charged to a backmixed autoclave. The volume of catalyst is measured in a 1" I.D. graduated cylinder after tapping the cylinder several times to thoroughly pack the catalyst. The weight of the catalyst is noted.

2. The backmixed autoclave is heated to about reaction temperature in a nitrogen flow of 20 SCFH with the fan operating at 1500 rpm. The nitrogen flow is then discontinued and the above-described feed stream is introduced into the reactor. The total gas outlet flow is adjusted to 22.6 SCFH. The temperature is adjusted over the next few hours so that the ethylene oxide concentration in the outlet gas is approximately 1.0%

3. The outlet oxide concentration is monitored over the next 4–6 days to make certain that the catalyst has reached its peak steady state performance. The temperature is periodically adjusted to achieve 1% outlet oxide. The selectivity of the catalyst to ethylene oxide and the temperature are thus obtained.

The standard deviation of a single test result reporting catalyst efficiency in accordance with the procedure described above is 0.7% efficiency units.

Tables II through VI below summarize test results obtained with silver catalysts in the absence of additives and those containing cesium in combination with one or more alkali metals selected from among lithium, sodium, potassium and rubidium. Tests were carried out using a variety of catalyst carriers and different preparation procedures. Catalysts which were prepared by the same method of preparation on a similar carrier are identified in the Tables by a common number

TABLE II

| EXPERIMENT | Wt. % Ag | Wt. % Cs | Wt. % K | % EFF.** | TEMP. (°C.) |
|---|---|---|---|---|---|
| 1 A | 11.14 | 0.00479 | 0.0000 | 71.7 | 256 |
| 1 B | 11.14 | 0.00477 | 0.00158 | 73.9 | 256 |
| 1 C | 10.89 | 0.00461 | 0.00450 | 75.4 | 256 |
| 1 D | 10.41 | 0.0000 | 0.0000 | 68.4 | 265 |
| 1 E | 10.80 | 0.0000 | 0.00613 | 69.9 | 261 |
| 1 F | 10.93 | 0.0000 | 0.0123 | 73.3 | 264 |
| 1 G | 10.90 | 0.0000 | 0.0210 | 66.6 | 299 |
| 1 H | 11.04 | 0.00941 | 0.0000 | 75.6 | 256 |
| 1 I | 11.06 | 0.00941 | 0.00313 | 76.9 | 258 |
| 1 J | 10.92 | 0.0186 | 0.0000 | 73.1 | 283 |
| 1 K | 11.16 | 0.0191 | 0.00633 | 72.0 | 293 |
| 1 L | 8.04 | 0.004 | 0.008 | 76.0 | 269.3 |
| 1 M | 7.84 | — | 0.0078 | 75.0 | 263.8 |
| 1 N | 8.28 | 0.0041 | — | 73.8 | 258.3 |
| 1 O | 8.07 | — | — | 67.3 | 260.0 |
| 1 P | 14.97 | — | — | 66.7 | 252.9 |
| 1 Q | 15.19 | 0.00405 | — | 72.6 | 252.0 |
| 1 R | 14.80 | — | 0.0079 | 75.5 | |
| 1 S | 15.10 | 0.004 | 0.0081 | 77.9 | 256.6 |
| 2 A | 17.4 | 0.000 | 0.093 | 73.5 | 278 |
| 2 B | 16.6 | 0.0044 | 0.088 | 74.7 | 279 |
| 2 C | 16.5 | 0.0085 | 0.089 | 74.2 | 278 |
| 2 D | 17.3 | 0.000 | 0.000 | 68–67* | 28–299 |
| 2 E | 17.0 | 0.0044 | 0.0016 | 70.8 | 276 |
| 2 F | 15.7 | 0.0044 | 0.069 | 74.1 | 280 |
| 2 G | 16.5 | 0.0092 | 0.0028 | 72.2 | 275 |
| 2 H | 16.5 | 0.0092 | 0.088 | 73.2 | 287 |

*Due to rapid deactivation of this catalyst, initial and final performances, respectively, are given
**"EFF" is the abbreviation for efficiency as previously defined.

Experiments 1B and 1C demonstrate the synergism achieved with silver catalysts containing mixtures of cesium and potassium in accordance with the invention relative to the "cesium only" catalyst of 1A which contained essentially the same concentration of silver and cesium but contained no potassium. As used herein, the term "cesium only" refers to a catalyst wherein cesium is the only alkali metal deposited upon the carrier. The terms "potassium only", "lithium only", and "sodium only" are correspondingly defined for the respective catalysts. Thus, the efficiency achieved with combination of alkali metals in experiment 1B was about 2% higher than that achieved with the corresponding cesium only catalyst of experiment 1A. The further addition of K from a level of 0.00158% (Example 1B) to a level of 0.0045% K (experiment 1C) while maintaining Ag and Cs essentially constant provided an even greater improvement in efficiency relative to 1A, namely, about 3.7%. The catalyst of experiment 1D contained no cesium or potassium and provided a relatively low 68.4% efficiency. Experiments 1E, F, and G demonstrate that "potassium only" catalysts which contained essentially the same amount of silver as catalysts 1B and 1C achieved a selectivity no higher than 73.3%, significantly below that achieved with the catalysts of 1B and 1C containing mixtures of cesium and potassium. It should also be noted that in addition to providing higher efficiency, the catalysts of the invention (1B and 1C) operated at lower temperatures than the potassium only catalysts (1E, 1F and 1G), thus indicating higher catalyst activity. Although the cesium only catalyst (1A) operated at the same low temperature as catalysts 1B and C, it provided a substantially lower efficiency.

The catalyst of experiment 1H was a cesium only catalyst containing Cs at a level nearly double that of catalysts 1A, B and C. The addition of 0.0031% potassium to a catalyst of such composition produced an efficiency improvement of greater than 1% as shown in Example 1.

Experiments 1J and 1K are illustrative of a non-synergistic combination of Cs and K. Thus, the addition of K to the cesium only catalyst of 1J containing about 11% Ag and a relatively high Cs concentration of 0.0186% resulted in a catalyst (1K) having a lower efficiency and higher operating temperature. That is to say, the combination of K and Cs in experiment 1K did not produce a synergistic result. Consequently, such cesium potassium mixture is not in accord with the present invention.

Experiments 1L through 1O demonstrate the synergism of the present invention for catalysts containing approximately 8% silver. The efficiency of catalyst 1L which contained a synergistic combination of cesium and potassium was 1% higher than the potassium only catalyst of 1M, and more than 2% higher than the efficiency of the cesium only catalyst of 1N. Silver catalyst 1O which contained no cesium or potassium achieved an efficiency nearly 9% below that of catalyst 1L.

Experiments 1P through 1S demonstrate the synergism of the present invention for catalyst containing approximately 15% silver. The efficiency of catalyst 1S which contained a synergistic mixture of cesium and potassium was more than 5% higher than the cesium only catalyst of 1Q which contained the respective amount of cesium in such mixture, and about 2.5% higher than the potassium only catalyst of 1R which contained the respective amount of potassium in such mixture. Catalyst 1P which contained no additives achieved an efficiency about 11% lower than catalyst 1S.

Experiments 2B and 2C demonstrate the efficiencies achieved with potassium-cesium mixtures for a catalyst containing about 17% silver compared to the potassium only catalyst of experiment 2A. The addition of .0044% cesium in experiment 2B resulted in an improved efficiency of 74.7% compared to the 73.5% efficiency achieved in experiment 2A. The silver catalyst of 2D which had no alkali metal deposited on the carrier is provided in the Table for comparative purposes.

A comparison of experiments 2E and 2F show that when the K concentration was increased from 0.0016% to 0.069% while maintaining the Cs level constant, a greater than 3% improvement in efficiency was achieved. Likewise, a comparison of experiments 2G and 2H demonstrates that when the potassium concentration was increased while maintaining the silver and cesium levels constant, a 1% improvement in efficiency resulted.

Three catalysts containing 7% Ag were prepared containing the optimum cesium concentration as determined from the Efficiency Model, supra, obtained from a designed set of experiments. The catalysts (experiments 3A, B and C) all contained about 7.0 wt. % silver and 0.00906 wt. % cesium, with no potassium being present. To demonstrate the operation of the Efficiency Model, three additional catalysts were prepared (experiments 3D, E and F), each containing about 7.0% silver, 0.00906% cesium and 0.004% potassium. The difference in the performance of the cesium/potassium catalysts relative to the cesium only catalysts was predicted from the Efficiency Model to be about 0.6% efficiency units. As noted below in Table III, the actual observed difference in performance was found to be 0.7%, which is regarded to reflect agreement with the prediction of the Efficiency Model. Experiment 3G provides the efficiency of a potassium only catalyst containing silver and potassium at the same concentration as the catalysts of experiments 3D, E and F, thus demonstrating the synergism achieved with the cesium-potassium combination.

TABLE III

| Experiment | % Eff. | T, °C. |
|---|---|---|
| Cesium Only Catalysts: 7.0% Ag, 0.00906% Cs | | |
| 3A | 75.4 | 263.9 |
| 3B | 75.7 | 261.4 |
| 3C | 75.4 | 266.1 |
| Average: 75.5 ± 0.17* | | |
| Cesium Plus Potassium Catalysts: 7.0% Ag, 0.00906% Cs, 0.004% K | | |
| 3D | 76.0 | 271.4 |
| 3E | 76.1 | 271.5 |
| 3F | 76.4 | 270.9 |
| Average: 76.2 ± 0.21* | | |
| Potassium Only Catalyst: 7.0% Ag, 0.0040% K | | |
| 3G | 72.8 | 265.3 |

*Values reflect standard deviations.

Table IV below demonstrates the synergism achieved with a combination of cesium and lithium (experiment 4C) relative to the corresponding cesium only catalyst of experiment 4A and the corresponding lithium only catalyst of experiment 4B. Thus, the catalyst of 4C was about 10% more efficient than the lithium only catalyst of 4B and about 3.5% more efficient than the cesium only catalyst of 4A.

Experiment 4D demonstrates that when the lithium concentration of catalyst 4C was increased about tenfold, the resulting efficiency was reduced by more than 3%. However, a comparison of catalysts 4D and 4E discloses that the efficiency obtained with catalyst 4D was increased by increasing the cesium concentration from 0.0053% to 0.0300%. It should be noted that the cesium only catalyst of experiment 4G (corresponding to the cesium concentration of 4E) was inactive; that is, at that concentration of cesium, no ethylene oxide was produced. Yet, the combination of this concentration of cesium with 0.0300% lithium resulted in a very active catalyst (4E). Similarly, the lithium only catalyst of 4F (corresponding to the lithium concentration of 4E) provided a relatively low efficiency of 65.4%. Thus, the synergism achieved in catalyst 4E is underscored by the sharp contrast of its efficiency relative to the poor results achieved with catalysts 4F and 4G.

TABLE IV

CATALYSTS CONTAINING SYNERGISTIC COMBINATIONS OF SILVER, CESIUM AND LITHIUM

| Experiment | Wt. % Ag | Wt. % Cs | Wt. % Li | % Eff. | Temp. (°C.) |
|---|---|---|---|---|---|
| 4A | 12.8 | 0.0052 | 0.000 | 7.26 | 257 |
| 4B | 13.1 | 0.000 | 0.0030 | 65.9 | 267 |
| 4C | 12.8 | 0.0052 | 0.0030 | 76.0 | 257 |
| 4D | 13.1 | 0.0053 | 0.0302 | 72.8 | 258 |
| 4E | 13.0 | 0.0300 | 0.0300 | 78.6 | 258 |
| 4F | 13. | 0.000 | 0.0030 | 65.4 | 263 |
| 4G | 13.0 | 0.0300 | 0.000 | Inactive* | |

*No measurable ethylene oxide was produced.

Table V below demonstrates the synergism achieved with the catalyst of experiment 5C relative to the corresponding cesium only catalyst of experiment 5A and the corresponding sodium only catalyst of experiment 5B. Thus, the catalyst of 5C was 6% more efficient than the cesium only catalyst of 5A and 7.2% more efficient than the sodium only catalyst of 5B. Experiment 5D discloses that increasing the sodium concentration ten-fold relative to the concentration in catalyst 5C had the effect of lowering the catalyst efficiency.

TABLE V

CATALYSTS CONTAINING SYNERGISTIC COMBINATIONS OF SILVER, CESIUM AND SODIUM

| Experiment | Wt. % Ag | Wt. % Cs | Wt. % Na | % Eff. | Temp. (°C.) |
|---|---|---|---|---|---|
| 5A | 12.8 | 0.005 | 0.000 | 72.6 | 257 |
| 5B | 13.0 | 0.000 | 0.010 | 71.4 | 259 |
| 5C | 13.0 | 0.005 | 0.010 | 78.6 | 251 |
| 5D | 12.4 | 0.005 | 0.100 | 77.6 | 263 |

Table VI below demonstrates the synergism achieved with a catalyst containing silver and cesium in combination with potassium, sodium and lithium as indicated in experiment 6A. The presence of chloride ion in the catalyst concentrations of 6A, B and C indicates that at least a portion of the alkali metal salts used in the catalyst preparation procedure were in the form of chlorides. The efficiency achieved with the synergistic combination of experiment 6A was about 1.2% greater than the efficiency of the corresponding cesium only catalyst of 6C and about 9% greater than the corresponding combination of potassium, sodium and lithium of catalyst 6B.

TABLE VI

CATALYST CONTAINING SYNERGISTIC COMBINATION OF SILVER, CESIUM POTASSIUM, SODIUM AND LITHIUM

| Experiment | Wt. % Ag | Wt. % Cs | Wt. % K | Wt. % Na | Wt. % Li | Wt. % Cl | % Eff. | Temp. (°C.) |
|---|---|---|---|---|---|---|---|---|
| 6A | 13.1 | 0.0132 | 0.001 | 0.002 | 0.006 | 0.0137 | 78.4* | 262 |
| 6B | 13.00 | 0.000 | 0.001 | 0.002 | 0.006 | 0.0137 | 69.4 | 267 |
| 6C | 13.1 | 0.0132 | 0.000 | 0.000 | 0.000 | 0.0035 | 77.2 | 265 |

*The efficiency represents the average of two experiments.

The catalysts of the invention can be prepared with a variety of carriers and preparation procedures. The defined synergism obtainable with combinations of cesium with the other alkali metals is not restricted, for example, to a particular type or chemical composition of catalyst carrier, to a particular sequence of silver and alkali metal deposition, or to a special class of solvents or solubilizing agents used in the preparation procedure.

In the following examples detailed procedures are provided as illustrative of methods and carriers which are useful for preparing catalysts according to the invention. These examples are by way of illustration only, and are not to be construed as limiting the scope of the invention described herein.

EXAMPLE 1

A catalyst containing 11.14 wt. % Ag, 0.00477 wt. % Cs and 0.00158 wt. % K was prepared as hereinafter described on an alpha-alumina carrier "A" having the following chemical composition and physical properties:

| Chemical Composition of Carrier "A" | |
|---|---|
| Alpha-Alumina | 98.5 wt % |
| Silicon Dioxide | 0.74 wt % |
| Calcium Oxide | 0.22 wt % |
| Sodium Oxide | 0.16 wt % |
| Ferric Oxide | 0.14 wt % |
| Potassium Oxide | 0.04 wt % |
| Magnesium Oxide | 0.03 wt % |

| Physical Properties of Carrier "A" | |
|---|---|
| Surface Area (1) | ~0.3 m²/g |
| Pore Volume (2) (or water absorption) | ~0.50 cc/g |
| Packing Density (3) | 0.70 g/ml |
| Median Pore Diameter (4) | 21 microns |

| Pore Size Distribution, % Total Pore Volume (4) | |
|---|---|
| Pore Size, Microns | % TPV |
| 0.1–1.0 | 1.5 |
| 1.0–10.0 | 38.5 |
| 10.0–30.0 | 20.0 |
| 30–100 | 32.0 |
| >100 | 8.0 |

(1) Method of measurement described in "Adsorption, Surface Area and Porosity", S.J. Gregg and K S.W. Sing, Academic Press (1967), pages 316–321.
(2) Method of Measurement as described in ASTM C20–46.
(3) Calculated value based on conventional measurement of the weight of the carrier in a known volume container.
(4) Method of measurement described in "Application of Mercury Penetration to Materials Analysis", C.Orr Jp., Powder Technology, Vol. 3, pp. 117–123 (1970).

The carrier "A" was impregnated under vacuum as hereinafter described with a solution of silver salts and alkali metals. The impregnating solution was prepared at a concentration such that the finished catalyst contained the desired amounts of silver, cesium and potassium. The required concentration of silver, cesium and potassium in solution for the given carrier is calculated from the packing density (grams/cc) and pore volume of the carrier which are either known or readily determined Assuming that all of the silver in the impregnating solution contained in the pores of the carrier is deposited upon the carrier, approximately 21 wt. % silver in solution is necessary to prepare a catalyst containing about 11 wt. % silver on the catalyst. The required concentration of alkali metal in solution is obtained by dividing the solution silver concentration by the ratio of silver to cesium or potassium desired in the finished catalyst Thus, to obtain 11.0 wt. % Ag and 0.0047 wt. % Cs, the ratio is approximately 2330 and the required cesium concentration in solution is 0.009 wt. %. In like manner, the solution concentration of potassium was calculated to be 0.003 wt. %. The solution containing the desired concentrations of silver and alkali metals was prepared as described below:

IMPREGNATING SOLUTION PREPARATION 80.16 gms of ethylenediamine (high purity grade) was mixed with 176 g of distilled water. 60.06 gms of anhydrous oxalic acid (reagent grade) was then added slowly to the solution at ambient temperature(23° C.) while continuously stirring. During this addition of oxalic acid, the solution temperature rose to about 40° C. due to the reaction exotherm. 147.25 gms. of silver oxide power (Handy and Harmon, 850 Third Avenue, New York, N.Y. 10022) was then added to the diamine-oxalic acidwater solution. Finally, 29.30 gms. of monoethanolamine, 13.26 gms. of aqueous Cs solution as hydroxide (0.00444 g Cs/ml soln, or 0.0589 g Cs), 34.28 gms. of aqueous K solution as carbonate 0.0005669 K/ml soln, or 0.0194 gms. K) and 120.6 gms. of distilled water were added to complete the solution. The solution was filtered and 0.9 grams of undissolved silver was recovered. The specific gravity of the resulting solution was about 1.328 g/ml.

CATALYST PREPARATION 125 g of Carrier "A" was impregnated in a 12" long×2" I.D. glass cylindrical vessel equipped with a side arm and suitable stopcocks for impregnating the carrier under vacuum. A 500 ml separatory funnel for containing the impregnating solution was inserted through a rubber stopper into the top of the impregnating vessel. The impregnating vessel containing the carrier was evacuated to approximately 2 inches of mercury pressure for about 20 minutes after which the impregnating solution was slowly added to the carrier by opening the stopcock between the separatory funnel and the impregnating vessel until the carrier was completely immersed in solution, the pressure within the vessel being maintained at approximately 2 inches of mercury. Following addition of the solution, the vessel was opened to the atmosphere to attain atmospheric pressure, the carrier then retaining immersed in the impregnating solution at ambient conditions for about 1 hour, and thereafter drained of excess solution for about 30 minutes. The impregnated carrier was then heat treated as follows to effect reduction of silver salt and deposition of cesium and potassium ions on the catalyst surface. The impregnated carrier was spread out in a single layer on a 2-⅜" wide endless stainless steel belt (spiral weave) and transported through a 2"×2" square heating zone for 2.5 minutes, the heating zone being maintained at 500° C. by passing hot air upward through the belt and about the catalyst particles at the rate of 266 SCFH. The hot air was generated by passing it through a 5 ft. long×2" I.D. stainless steel pipe which was externally heated by an electric furnace (Lindberg TM tubular furnace.. 2-½" I.D., 3 feet long heating zone) capable of delivering 5400 watts. The heated air in the pipe was discharged from a square 2"×2" discharge port located immediately beneath the moving belt carrying the catalyst carrier. After being roasted in the heating zone, the finished catalyst was weighed, and based upon the weight gain of the carrier, and the known ratios of silver to cesium and potassium in the impregnating solution, it was calculated to contain 11.14 wt. % of silver, 0.00477 wt. % cesium and 0.00158 wt. % potassium. By chemical analysis, described below, this catalyst was found to contain 10.88% Ag, in close agreement with the calculated value.

The analysis for silver was carried out by the following method: An approximately 50 g sample of catalyst was powdered in a mill and 10 g of the powdered sample weighed to the nearest 0.1 mg. The silver (and cesium, etc.) in the catalyst sample was dissolved in hot (80° C.) 50%, by volume, nitric acid solution. The insoluble alumina particles were filtered and washed with distilled water to remove all adhering nitrate salts of Ag, Cs, etc. This solution was made up to 250 ml in a volumetric flask using distilled water. A 25 ml aliquot of this solution was titrated according to standard procedures using a 0.1 Normal solution of ammonium thiocyanate and ferric nitrate as indicator. The amount of Ag so determined in 250 ml solution was then used to calculate the weight percent silver in the catalyst sample.

Silver and alkali metal concentrations for all catalysts described in the specification are calculated values as described above.

EXAMPLE 2

A catalyst containing 16.6 wt. % Ag, 0.0044 wt. % Cs and 0.088 wt. % K was prepared as hereinafter described on a carrier "B" having the following characteristics:

| Chemical Composition of Carrier "B" | |
|---|---|
| Alpha-Alumina | 86.0 wt % |
| Silicon Dioxide | 11.8 wt % |
| Calcium Oxide | 0.24 wt % |
| Sodium Oxide | 0.69 wt % |
| Ferric Oxide | 0.30 wt % |
| Potassium Oxide | 0.54 wt % |
| Titanium Dioxide | 0.34 wt % |
| Physical Properties of Carrier "B" | |
| Surface Area (1) | 0.10 m²/g |
| Pore Volume (2) | |
| (or water absorption | 0.40 cc/g |
| Packing Density (3) | 0.72 g/ml |
| Median Pore Diameter (4) | 22 microns |
| Pore Size Distribution (4) | |
| Pore Size, microns | % Total Pore Volume |
| 0.1–1.0 | 0.0 |
| 1.0–10.0 | 12 |
| 10.0–30 | 55 |
| 30–100 | 33 |
| >100 | 0.0 |

(1) Method of measurement described in "Adsorption, Surface Area and Porosity", S. J. Gregg and K. S. W. Sing, Academic Press (1967), pages 316–321.
(2) Method of Measurement as described in ASTM C20-46.
(3) Calculated value based on conventional measurement of the weight of the carrier in a known volume container.
(4) Method of measurement described in "Application of Mercury Penetration to Materials Analysis", C. Orr Jr., Powder Technology, Vol. 3, pp. 117–123 (1970).

The preparation procedure consisted on the following steps:
(i) 333.5 g of lactic acid (88% in water) was heated to about 75° C. and 1.44 g K2C03 and 4.86 g of aqueous C50H solution (containing 0.008 g/ml or 0.039 g Cs) added to the heated lactic acid, while stirring the solution.
(ii) 163.75 g $Ag_2O$ (Metz Metallurgical Corp., 3900 So. Clinton Ave., So. Plainfield, N.J. 07080) was incrementally added to the heated lactic acid with stirring so that the heat generated from the exothermic reaction of $Ag_2O$ with lactic acid did not exceed about 85° C. Most $Ag_2O$ and/or silver was left suspended in solution. This suspension was dark brownish grey in color.
(iii) Hydrogen peroxide (3.3 ml.) was incrementally added to the above $Ag_2O$ lactic acid solution while rapidly stirring to assist complete dissolution of the suspended matter. A clear yellow solution was obtained, the solution temperature being about 80° C. (Small amounts of lactic acid or water were added to make up for any evaporation losses.) This solution contained about 30.4% silver, 0.12% K and 0.0078% Cs.
(iv) 189 grams of carrier "B" was evacuated and impregnated with the solution prepared in (iii) while it was at its elevated temperature of about 80° C. The method of impregnating the carrier was as described in Example 1 with an additional step being that the cylindrical impregnating vessel containing the carrier was surrounded by a heating jacket which maintained the carrier temperature at about 80° C. during the impregnation procedure to insure that silver lactate remained in solution.
(v) The impregnated carrier of (iv) was heat treated at 400° C. for four minutes using the apparatus and general method described in Example 1.

EXAMPLE 3

A catalyst containing 13.4 wt. % Ag, 0.0091 wt. % Cs and 0.0027 wt. % K was prepared by the following procedure on Carrier "A"(described in Example 1).

Impregnating Solution Preparation 78.6 grams of triethylenetetramine (high purity grade) was mixed with 80 g of distilled water. 51.57 grams of oxalic acid dihydrate (reagent grade) was then added slowly to the continuously stirred amine solution. During this addition, the temperature of the solution increased to 60° C. due to the reaction exotherm. 5.83 g of aqueous cesium hydroxide solution (0.009728 g Cs/g solution) and 4.46 g of aqueous potassium carbonate solution (0.00369 of K/g solution) were then added to the solution followed by the addition of 89.26 g of silver oxide (Metz Metallurical Corp.). Finally 15.28 g of monoethanolamine was added to the solution along with additional distilled water to produce a total solution volume of 250 ml. The solution was filtered and about 5 g of undissolved silver was recovered.

Catalyst Preparation 150 g of Carrier "A" was evacuated at room temperature and impregnated with the above-described impregnation solution in accordance with the procedure of Example 1. Following impregnation, heat treatment of the carrier was carried out at 500° C. for 2.5 minutes using the apparatus and method described in Example 1.

The composition of the finished catalyst, calculated from the weight gain of the carrier, was as stated above.

EXAMPLE 4

A catalyst containing 13.04 wt. % Ag, 0.0089 wt. % Cs and 0.0026 wt. % K was prepared by the following procedure on carrier "A"(described in Example 1).

Impregnating Solution Preparation 114.25 grams of aminoethylethanolamine (high purity grade) was mixed with 80 g. of distilled water. 50.42 grams of oxalic acid dihydrate (reagent grade) was then slowly added to the continuously stirred amine solution, the solution temperature rising to about 60° C. due to the reaction exotherm. 5.84 g. of aqueous cesium hydroxide solution (0.009723 g Cs/g solution) and 4.52 g of aqueous potassium carbonate solution (0.00369 g K/g solution) were then added to the solution followed by the addition of 89 g of silver oxide (Metz Metallurgical Corp.). Additional distilled water was then added to the solution to produce a total volume of 250 ml.

Catalyst Preparation 150 g of carrier "A" was evacuated and impregnated with the above-described solution in accordance with the procedure of Example 1. Heat treatment of the impregnated carrier was then carried out at 500° C. for 2.5 minutes using the apparatus and method as described in Example 1.

EXAMPLE 5

A catalyst having nominally the same composition as the catalyst of Example 1 (specifically, 11.1 wt. % Ag, 0.0048 wt. % Cs and 0.0016 wt. % K) was prepared as described in Example 1 except that the preparation of the impregnating solution was carried out using aqueous solutions of cesium chloride and potassium chloride instead of cesium hydroxide and potassium carbonate, respectively. Upon addition of such chloride salts to the silver-containing impregnating solution, the solution remained clear, i.e., no precipitation of silver chloride was observed.

EXAMPLE 6

A catalyst having nominally the same composition as the catalyst of Example 1 except for the substitution of lithium for potassium (specifically 11.0 wt. % Ag, 0.0047 wt. % Cs and 0.003 wt. % Li) was prepared as described in Example 1, the solution concentration of lithium being calculated to be 0.00573 wt. %. Accordingly, the preparation procedure of Example 1 was followed except that instead of adding potassium carbonate solution to the impregnating solution, 34 grams of an aqueous lithium solution as carbonate (0.001094 g lithium/ml, or 0.0372 g lithium) were added.

EXAMPLE 7

A catalyst having nominally the same composition as the catalyst of Example 1 except for the substitution of sodium for potassium (specifically 11.0 wt. % Ag, 0.0047 wt. % Cs and 0.01 wt. % sodium) was prepared in accordance with the procedure of Example 1, the solution concentration of sodium being calculated to be 0.0191 wt. %. Thus, the procedure of Example 1 was followed except that instead of adding potassium carbonate to the impregnating solution, 34 grams of an aqueous sodium solution as carbonate (0.00365 g sodium/ml, or 0.12415 gram sodium) were added.

EXAMPLE 8

A catalyst containing 12.59 wt. % Ag, 0.0088 wt. Cs and 0.0025 wt. % K was prepared on Carrier "A" (described in Example 1) by a sequential impregnation method whereby potassium and cesium were deposited upon the carrier prior to the deposition of silver, as follows: 146.1 grams of Carrier "A" was impregnated with 250 ml of an aqueous solution containing 0.05696 g of cesium as hydroxide and 0.1674 g of potassium as carbonate following the general method of impregnation described in Example 1. The impregnated carrier was then heat treated at 400° C. for 2.5 minutes in accordance with the procedure of Example 1 to deposit cesium and potassium ions on the carrier surface. Following this heat treatment, the carrier was impregnated with the silver-containing impregnating solution as described below:

Preparation of Silver-Containing Impregnating Solution 48.9 grams of ethylenediamine (high purity grade) was mixed with 80 cc of distilled water. 50.6g of oxalic acid dihydrate (reagent grade) was then added slowly to the solution over a period of one hour while continuously stirring During this addition of oxalic acid, the solution temperature rose to about 40° C. due to the reaction exotherm. 89.34 grams of silver oxide powder (Metz Metallurgical Corp.) was then added to the diamineoxalic acid-water solution. Finally, 17.84grams of monoethanolamine was added to the solution along with additional distilled water to provide a total solution volume of 250 ml.

CATALYST PREPARATION

The aforementioned Carrier "A" was impregnated with the above-described impregnating solution and then heat treated at 400° C. for 2.5 minutes in accordance with the method described in Example 1.

EXAMPLE 9

A catalyst containing 13.09 wt. % Ag, 0.0089 wt. % Cs and 0.0026 wt. % K was prepared on Carrier "A" (described in Example 1) by a sequential impregnation method whereby silver was deposited upon the carrier prior to the deposition of potassium and cesium, as follows:

Preparation of Silver-Containing Impregnating Solution 48.43 grams of ethylenediamine (high purity grade) was mixed with 100 grams of distilled water. 50.75 grams of oxalic acid dihydrate (reagent grade) was then added slowly to the solution at ambient temperature while continuously stirring, the solution temperature rising to about 60° C. due to the reaction exotherm. 88.97 grams of silver oxide power (Metz Metallurgical Corp.) was then added to the diamine-oxalic acid-water solution. Finally 17.7 grams of monoethanolamine and 44.0 grams of distilled water were added to complete the solution The specific gravity of the solution was 1.3957.

Catalyst Preparation 150 grams of Carrier "A" was impregnated with the above-described solution and then heat treated at 500° C. for 2.5 minutes in accordance with the method described in Example 1. Following this heat treatment, the carrier was impregnated with the impregnating solution as described below:

Preparation of Impregnating Solution Containing Cesium and Potassium 5.791 grams of aqueous cesium hydroxide solution (0.009723 grams Cs/g solution) and 4.415 grams of aqueous potassium carbonate solution (0.00369 grams K/g solution) were added to a 250 ml volumetric cylinder and n-butanol then added to fill the cylinder to the 250 ml mark. The cylinder was heated to 40° C., sealed and shaken vigorously until a clear solution was obtained.

Catalyst Preparation

The above described silver-containing Carrier "A" was impregnated under vacuum with the impregnating solution containing cesium and potassium for a period of 15 minutes, and then drained of excess solution using the method described in Example 1 Heat treatment of the carrier was then carried out at 500° C. for 2.5 minutes in accordance with the method of Example 1.

What is claimed is:

1. In the continuous process for the production of ethylene oxide by the vapor phase oxidation of ethylene with molecular oxygen provided as an oxygen-containing gas at a temperature of from about 200° C. to 300° C. in the presence of at least about one mole percent of carbon dioxide and an organic chloride in the gaseous feed stream and in the presence of a supported, silver-containing catalyst in a fixed bed, tubular reactor used in commercial operations to form ethylene oxide, wherein said supported, silver-containing catalyst contains 2 to 20 weight percent silver deposited on a support which is in a form and size for use in the reactor, wherein (i) the specific reaction conditions of the ethylene oxide process; (ii) the specific catalyst support characteristics and (iii) the specific silver deposition method comprise an ethylene oxide production system, the improvement in which the catalyst comprises silver deposited on an alpha-alumina macroporous support in a first amount having a surface area less than 10 $m^2/g$ and contains a combination of (a) cesium in a second amount and (b) at least one other alkali metal selected from the group consisting of lithium, sodium, potassium and rubidium in a third amount, which combination comprises (a) and (b) in amounts in relation to the amount of silver in the catalyst sufficient to provide an efficiency of ethylene oxide manufacture that is greater than the efficiencies obtainable in the same ethylene oxide production system, including the same conversions, than (i) a second catalyst containing silver in the first amount and cesium in the second amount, and (ii) a third catalyst containing silver in the first amount and the alkali metal in the third amount, wherein the combination of silver, cesium and alkali metal in said catalyst is characterizable by an efficiency equation:

$$\text{efficiency \%} = b_0 + b_1(BG) + b_2(BCs) + \sum_{1}^{4} b_{3j} BA_j + b_4(BG)^2 + b_5(BCs)^2 + \sum_{1}^{4} b_{6j} BA_j^2 + b_7 (BG \cdot BCs) + (BG) \sum_{1}^{4} b_{8j} BA_j + (BCs) \sum_{1}^{4} b_{9j} BA_j,$$

where
$BA_1 = BRb$,
$BA_2 = BK$,
$BA_3 = BNa$,
$BA_4 = BL_i$, and where the coefficient $b_0$ through $b_{9j}$ and BG, BRb, BK, BNa, BLi and BCs are determined from a composite design set of experiments using the same ethylene oxide production system for the independent variables silver, cesium and alkali metal, and wherein BG is the difference of the average value of the silver content from the silver content used in the design set, BCs is the difference of the average value of the cesium content from the cesium content used in the design set, BRb is the difference of the average value of the rubidium content from the rubidium content used in the design set, BK is the difference of the average value of the potassium content from the potassium content used in the design set, BNa is the difference of the average value of the sodium content from the sodium content used in the design set and BLi is the difference of the average value of the lithium content from the lithium content used in the design set.

2. The process of claim 1 wherein said catalyst contains silver in an amount of from about 6% to about 16% by weight.

3. The process of claim 1 wherein said alkali metal is sodium.

4. The process of claim 1 wherein said alkali metal is lithium.

5. The process of claim 1 wherein said alkali metal is potassium.

6. The process of claim 1 wherein said alkali metal is rubidium.

7. The process of claim 5 wherein cesium and potassium are present in a weight ratio of from about 100:1 to about 1:100.

8. The process of claim 1 wherein the surface area of the catalyst support is less than about 1 meter square per gram.

9. The process of claim 1 wherein the pore volume of the support is from about 0.2 to 0.6 cc/gram.

10. In the continuous process for the production of ethylene oxide by the vapor phase oxidation of ethylene with molecular oxygen provided as an oxygen-containing gas at a temperature of from about 200° C. to 300° C. in the presence of at least about one mole percent of carbon dioxide and an organic chloride in the gaseous feed stream and in the presence of a supported, silver-containing catalyst in a fixed bed, tubular reactor used in commercial operations to form ethylene oxide, wherein said supported, silver-containing catalyst contains 2 to 20 weight percent silver deposited on a support which is in a form and size for use in the reactor, wherein (i) the specific reaction conditions of the ethylene oxide process; (ii) the specific catalyst support characteristics and (iii) the specific silver deposition method comprise an ethylene oxide production system, the improvement in which the catalyst comprises silver deposited on an alpha-alumina macroporous support in a first amount having a surface area less than 10 m$^2$/g and contains a combination of (a) cesium in a second amount and (b) at least one other alkali metal selected from the group consisting of lithium, sodium, potassium and rubidium in a third amount, which combination comprises (a) and (b) in amounts in relation to the amount of silver in the catalyst sufficient to provide an efficiency of ethylene oxide manufacture that is greater than the efficiencies obtainable in the same ethylene oxide production system, including the same conversions, than (i) a second catalyst containing silver in the first amount and cesium in the second amount, and (ii) a third catalyst containing silver in the first amount and the alkali metal in the third amount, said efficiencies determined in a backmixed, bottom-agitated autoclave with inlet conditions of:

| Component | Mole % |
|---|---|
| Oxygen | 6.0 |
| Ethylene | 8.0 |
| Ethane | 0.50 |
| Carbon Dioxide | 6.5 |
| Nitrogen | Balance of Gas |
| Ethyl Chloride | 7.5 parts per million | with a pressure of 275 psig, total outlet flow of 22.6 SCFH, and reaction temperature adjusted to maintain 1.0 mole % ethylene oxide in the outlet gas, wherein the combination of silver, cesium and alkali metal in said catalyst is characterizable by an efficiency equation:

$$\text{efficiency \%} = b_0 + b_1(BG) + b_2(BCs) + \sum_1^4 b_{3j} BA_j + b_4(BG)^2 + b_5(BCs)^2 + \sum_1^4 b_{6j} BA_j^2 + b_7 (BG \cdot BCs) +$$

$$(BG) \sum_1^4 b_{8j} BA_j + (BCs) \sum_1^4 b_{9j} BA_j,$$

where
$BA_1 = BRb,$
$BA_2 = BK,$
$BA_3 = BNa,$
$BA_4 = BL_i$, and where the coefficients $b_0$ through $b_{9j}$ and BG, BRb, BK, BNa, BLi and BCs are determined from a composite design set of experiments using the same ethylene oxide production system for the independent variables silver, cesium and alkali metal, and wherein BG is the difference of the average value of the silver content from the silver content used in the design set, BCs is the difference of the average value of the cesium content from the cesium content used in the design set, BRb is the difference of the average value of the rubidium content from the rubidium content used in the design set, BK is the difference of the average value of the potassium content from the potassium content used in the design set, BNa, is the difference of the average value of the sodium content from the sodium content used in the design set and BLi is the difference of the average value of the lithium content from the lithium content used in the design set.

11. In the continuous process for the production of ethylene oxide by the vapor phase oxidation of ethylene with molecular oxygen provided as an oxygen-containing gas at a temperature of from about 200° C. to 300° C. in the presence of diluent and inhibitor and in the presence of a supported, silver-containing catalyst in a fixed bed, tubular reactor used in commercial operations to form ethylene oxide, wherein said supported, silver-containing catalyst contains 2 to 20 weight percent silver deposited on a support which is in a form and size for use in the reactor, the improvement wherein the catalyst comprises silver deposited on an alpha-alumina macroporous support in a first amount having a surface area less than 10 m$^2$/g and contains a combination of (a) cesium in a second amount and (b) at least one other alkali metal selected from the group consisting of lithium, sodium, potassium and rubidium in a third amount, which combination comprises (a) and (b) in amounts in relation to the amount of silver in the catalyst sufficient to provide an efficiency of ethylene oxide manufacture that is greater than the efficiencies obtainable from (i) a second catalyst containing silver in the first amount and cesium in the second amount, and (ii) a third catalyst containing silver in the first amount and the alkali metal in the third amount, said efficiencies determined in a backmixed, bottom-agitated autoclave with inlet conditions of:

| Component | Mole % |
|---|---|
| Oxygen | 6.0 |
| Ethylene | 8.0 |
| Ethane | 0.5 |
| Carbon Dioxide | 6.5 |
| Nitrogen | balance of gas |
| Ethylene Chloride | 7.5 parts per million | with a pressure of 275 psig, total outlet flow of 22.6 SCFH, and reaction temperature adjusted to maintain 1.0 mole % ethylene oxide in the outlet gas.

* * * * *